United States Patent [19]

Cornelius et al.

[11] 4,362,818

[45] Dec. 7, 1982

[54] ACYLATION OF *MUCOR PUSILLUS* MICROBIAL RENNET ENZYME

[75] Inventors: Dennis A. Cornelius, Elkhart, Ind.; Clifford V. Asmus, Niles, Mich.; Moshe M. Sternberg, Oakland, Calif.

[73] Assignee: Miles Laboratories, Inc., Elkhart, Ind.

[21] Appl. No.: 235,103

[22] Filed: Feb. 17, 1981

[51] Int. Cl.$^3$ .......................... C12N 9/58; C12N 9/96; A23C 19/032
[52] U.S. Cl. ...................................... 435/223; 426/63; 426/36; 435/188
[58] Field of Search ....................... 435/188, 222, 223; 426/36, 63

[56] References Cited

U.S. PATENT DOCUMENTS 3,212,905 10/1965 Arima et al. .......................... 426/36
3,886,042 5/1975 Blumberg et al. .................. 435/222
4,255,454 3/1981 Branner-Jorgensen .......... 426/63 X

*Primary Examiner*—David M. Naff
*Attorney, Agent, or Firm*—James D. McNeil

[57] ABSTRACT

A method for increasing the milk coagulating activity of microbial rennet obtained from *Mucor pusillus* microorganisms. The method involves acylating *Mucor pusillus* microbial rennet enzyme with maleic, citraconic, phthalic, cis-1,2-cyclohexanedicarboxylic, 1,2,4-benzenetricarboxylic, homophthalic, 3-nitro-phthalic, bromomaleic or dichloromaleic anhydride.

2 Claims, No Drawings

ACYLATION OF *MUCOR PUSILLUS* MICROBIAL RENNET ENZYME

BACKGROUND OF THE INVENTION

1. Field of the Invention

The production of cheese generally involves the steps of clotting or coagulating milk to form a curd, cutting the curd into pieces and cooking the curd. The cooked curd is then separated from residual whey, mixed with salt, and pressed and cured to form the desired cheese product. In the classical method of making cheese, rennet, an enzyme-containing preparation obtained from the fourth stomach of milk-fed calves, is used. Since rennet is derived from calves, the quantity of rennet available for cheesemaking is directly dependent upon the number of calves that are being processed for food purposes. This has prompted attempts in the prior art to develop suitable microbial enzyme preparations ("microbial rennets") to serve as substitutes for calf rennet. Several microbial rennet preparations have been developed. These are prepared, for example, from *Mucor pusillus* and *Mucor miehei*.

Enhancement of the milk coagulating activity of microbial rennet has been a continuing goal of research efforts.

2. Prior Art

Belgian Pat. No. 880870 claims a method for reducing the thermal stability of microbial rennet by acylating the rennet with a monocarboxylic acid acyl radical having from 1 to 6 carbon atoms. The applicant notes that during the cheesemaking process, the whey is recovered and pasteurized and utilized, e.g., as an additive to whole milk, to produce enriched milk. If the microbial rennet is thermally stable, pasteurized whey may still contain a level of proteolytic activity sufficient to produce undesirable protein coagulation.

The patentee of the Belgian Pat. No. 880870 acknowledges that acylation produces a loss of milk coagulating activity and places great emphasis on the importance of thermal destabilization over the importance of the coagulating activity of the microbial rennet produced. The patentee indicates that a destabilization of from 3°–5° C. with a coagulating activity loss up to 50 percent seems to be an appropriate compromise between the above-mentioned conflicting factors.

U.S. Pat. No. 3,886,042 describes the modification of proteolytic enzymes to increase the hydrolase activity by acylating with an acylating agent containing an amino acid residue, e.g., acetylalanyl, acetylphenylalanyl and β-phenylpropionylphenylalanyl. The patent does not disclose any data relating to milk coagulating activity.

The present invention discloses and claims a method of acylating microbial rennet obtained from *Mucor pusillus* with selected anhydrides whereby the milk coagulating activity of the enzyme can be increased over 100 percent. Neither of the above-referred-to patents disclose or suggest a method of increasing milk coagulating activity.

SUMMARY OF THE INVENTION

The present invention is directed to a method for increasing the milk coagulating activity of microbial rennet enzyme obtained from *Mucor pusillus*. The method involves acylating the microbial rennet with an acylating agent that is maleic, citraconic, phthalic, cis-1,2-cyclohexanedicarboxylic, 1,2,4-benzenetricarboxylic, homophthalic, 3-nitrophthalic, bromomaleic or dichloromaleic anhydride.

DETAILED DESCRIPTION OF THE INVENTION

The microbial enzyme used in the present invention can be obtained by methods known in the art, e.g., by growing a culture of *Mucor pusillus* under aerobic conditions in a medium containing appropriate nutrients. After culturing the microorganisms, the biomass is separated from the liquid and the microbial enzyme recovered. The microbial enzyme is then acylated with maleic, citraconic, phthalic, cis-1,2-cyclohexanedicarboxylic, 1,2,4-benzenetricarboxylic, homophthalic, 3-nitrophthalic, bromomaleic or dichloromaleic anhydride.

The process conditions for carrying out the present invention are not narrowly critical. Temperatures from about 0° to 35° C. can be employed. At temperatures below about 0° C., the enzyme solutions will tend to freeze. At temperatures above about 35° C., the microbial rennet will tend to become inactivated. Preferably, temperatures of about 5° to about 15° C. are employed. A pH of about 5 to about 10 can be employed. Preferably a pH of from 6 to 8 is employed.

Tests indicate that within a range of from less than 6 percent enzyme strength to 200 percent enzyme strength, from about 0.1 to 2 percent anhydride (w/v anhydride to volume enzyme solution) can be used. An increase in milk coagulating activity is obtained within this range, which varies with the identity of the anhydride used. Routine screening tests, by the method described in the Examples below, can be used to determine the optimum reaction conditions.

The following method is employed to measure the coagulating activity of the acylated and non-acylated *Mucor pusillus* microbial rennets.

Clotting Activity

A 10 percent (weight/volume basis) aqueous solution is prepared by dissolving the appropriate amount of non-fat dry milk solids in water. To this solution is then added $CaCl_2 \cdot 2H_2O$ to produce a concentration of 0.01 M calcium. A 5 ml-portion of the above milk solution is placed in a test tube and heated to 37.5° C. A 0.5 ml-portion of aqueous diluted enzyme at 37.5° C. is then added to the milk solution in the test tube. The enzyme-milk solution mixture is then agitated, and the time to form the first clot is measured. The enzyme concentration is selected so that the coagulating time will be between 0.5 and 4 minutes. The milk coagulating activity of the enzyme is calculated as follows:

$$\text{Soxhlet Units} = \frac{M \text{ (ml)}}{E \text{ (mg)}} \times \frac{2400 \text{ (sec)}}{T \text{ (sec)}} \times 1000$$

wherein:
M = milk volume
E = enzyme weight
T = time until first clot forms

The enzyme activity is then expressed in Soxhlet Units (SU) per gram. When the enzyme is originally employed in a liquid form, rather than dissolving powdered enzyme in water, the appropriate volume in microliters E is used in the above formula, and the enzyme activity is expressed as Soxhlet Units per milliliter. A Soxhlet Unit is the amount of enzyme activity that can clot 1 ml of the above milk solution in 40 min.

A microbial enzyme solution having a coagulating activity of 49,800 SU/ml is commonly described as "single strength" or as having "100 percent activity or strength".

Commercially available *Mucor pusillus* microbial rennet enzyme, obtained from Dairyland Food Laboratories, Waukesha, Wis. 53187, under the trade designation Emporase, was purchased and used in the following experiment.

EXAMPLE 1

A dilute solution (7.65 percent strength) of enzyme was prepared by adding 12.0 ml of *Mucor pusillus* (designated as having 127.5 percent strength) to 188 ml of 0.2 M sodium phosphate buffer (pH 7.0). Twenty ml-aliquot portions of this solution were cooled to about 5° C. in an ice-water bath. The aliquot portions were adjusted to a pH of about 7.5 with concentrated sodium hydroxide, and reacted incrementally with increasing amounts of maleic anhydride, while maintaining the pH at about 7.5 by titration with sodium hydroxide. The maximum amount of maleic anhydride added to an aliquot portion was 2 percent (w/v) (samples 6 and 12).

After the anhydride had been added and the base requirements had ceased as indicated by a stabilized pH, the reaction mixture was adjusted to pH 5.5 with glacial acetic acid and diluted to 100 ml with distilled water. The enzyme is more stable at pH 5.5.

The milk coagulating activities of the acylated microbial rennet were determined and compared with the milk coagulating activities of untreated microbial rennet, which was used as a control.

The results of two identical studies are summarized in Table 1 below and show the dramatic increases in milk coagulating activity that are produced by acylating *Mucor pusillus* microbial rennet with maleic anhydride.

TABLE 1

Reaction of *Mucor pusillus* Microbial Rennet Enzyme with Maleic Anhydride at 5° C.

| Sample | Anhydride Added (mg) | Increments of Anhydride Added | % Anhydride/Volume Enzyme (w/v) | Assay Time (sec) | % Original Activity |
|---|---|---|---|---|---|
| 1 | 0 | 0 | 0 | 55.75 | 100 |
| 2 | 20 | 1 × 20 mg | 0.10 | 50.5 | 110.4 |
| 3 | 50 | 1 × 50 mg | 0.25 | 47.5 | 117.4 |
| 4 | 100 | 1 × 100 mg | 0.5 | 41.0 | 135.4 |
| 5 | 200 | 2 × 100 mg | 1 | 29.25 | 190.6 |
| 6 | 400 | 4 × 100 mg | 2 | 30.5 | 182.8 |
| 7 | 0 | 0 | 0 | 62 | 100 |
| 8 | 20 | 1 × 20 mg | 0.10 | 53.5 | 115.9 |
| 9 | 50 | 1 × 50 mg | 0.25 | 50.5 | 122.8 |
| 10 | 100 | 1 × 100 mg | 0.50 | 42.5 | 145.9 |
| 11 | 200 | 2 × 100 mg | 1 | 33 | 187.9 |
| 12 | 400 | 4 × 100 mg | 2 | 34 | 182.4 |

EXAMPLE 2

The reaction procedure of Example 1 was repeated, except that the reactions were carried out at room temperature, about 20° to 22° C. The experimental results obtained are summarized in Table 2.

TABLE 2

Reaction of *Mucor pusillus* Microbial Rennet Enzyme with Maleic Anhydride at Room Temperature

| Sample | Anhydride Added (mg) | Increments of Anhydride Added | % Anhydride/Volume Enzyme (w/v) | Assay Time (sec) | % Original Activity |
|---|---|---|---|---|---|
| 13 | 0 | 0 | 0 | 66.75 | 100 |
| 14 | 20 | 1 × 20 mg | 0.10 | 56.5 | 118 |
| 15 | 50 | 1 × 50 mg | 0.25 | 41.25 | 162 |
| 16 | 100 | 1 × 100 mg | 0.5 | 31.5 | 212 |
| 17 | 200 | 2 × 100 mg | 1 | 30.25 | 221 |
| 18 | 400 | 4 × 100 mg | 2 | 35.75 | 187 |

As shown in Table 1 and Table 2, acylation of *Mucor pusillus* microbial rennet enzyme by treatment with maleic anhydride greatly increased the milk coagulating activity of the enzyme. Acylation of *Mucor pusillus* microbial rennet enzyme at room temperature appeared to increase the activity over the activity obtained by acylation at lower temperature.

Additional test results indicate that acylation with maleic anhydride yielded an enzyme having reduced proteolytic activity towards both acid- and urea-denatured hemoglobin. Reduction of proteolytic activity is desirable; as proteolytic activity increases, there can be an increase in the instances of development of off-flavors during the aging process in the cheese produced.

In Example 1 and Example 2, the maximum amount of maleic anhydride added to an aliquot sample, based on enzyme volume, was about 2 percent w/v. A noticeable increase in coagulating activity was obtained with the addition of as little as 20 mg (0.1 percent maleic anhydride); the maximum increase in coagulating activity was obtained at about 1 percent anhydride.

To determine the scope and nature of the acylating agents that are capable of producing increases in the milk coagulating activity of the *Mucor pusillus* microbial rennet enzyme, the reactions of the enzyme with several other acid anhydrides were investigated, as described in Example 3 below.

EXAMPLE 3

Dilute solutions of about 6 percent strength microbial rennet enzyme obtained from *Mucor pusillus* were cooled to about 5° C., and incremental amounts of the anhydrides listed in Table 3 below were added using a procedure similar to the procedure of Example 1. Depending on the water solubility of the acylating agent, it can be dissolved in varying amounts of acetone to improve the solubility. The milk coagulating activity of the acylated microbial rennet was determined and compared with the milk coagulating activity of untreated microbial rennet.

The experimental results obtained are summarized in Table 3 below.

TABLE 3

Reaction of *Mucor pusillus* Microbial Rennet Enzyme With Other Anhydrides at 5° C.

| Sample | cis-1,2-cyclohexanedicarboxylic anhydride added (mg) | Assay Time (sec) | % Original Activity |
|---|---|---|---|
| 19 | 0 | 69 | 100 |
| 20 | 20 | 61 | 113 |
| 21 | 50 | 51.5 | 133 |
| 22 | 100 | 40 | 173 |
| 23 | 200 | 40 | 173 |
| | phthalic anhydride added (mg) | | |
| 24 | 0 | 63 | 100 |
| 25 | 20 | 36 | 175 |

TABLE 3-continued

Reaction of *Mucor pusillus* Microbial Rennet Enzyme
With Other Anhydrides at 5° C.

| 26 | 50 | 43 | 147 |
| 27 | 100 | 117 | 54 |
| 28 | 200 | 384 | 16 |
| citraconic anhydride added (μl) | | | |
| 29 | 0 | 54 | 100 |
| 30 | 20 | 58 | 93 |
| 31 | 50 | 47.5 | 113.7 |
| 32 | 100 | 39 | 138.5 |
| 33 | 200 | 35.25 | 153.2 |
| 34 | 400 | 36.5 | 148.0 |

The above test results indicate that under the reaction conditions listed, acylation with cis-1,2-cyclohexanedicarboxylic, phthalic and citraconic (methylmaleic) anhydrides results in increases in milk coagulating activity of about 50 percent to 75 percent.

Similar procedures were carried out to determine the effect of other anhydrides on the milk coagulating activity of *Mucor pusillus* microbial rennet enzyme. The following maximum increases were obtained: 1,2,4-benzenetricarboxylic anhydride, 73 percent; homophthalic anhydride, 123 percent; 3-nitrophthalic anhydride, 45 percent; bromomaleic anhydride, 50 percent; dichloroacetic anhydride, 40 percent.

COMPARATIVE TEST RESULTS

The procedure described in Example 1 was used, and acylation with the following anhydrides was shown to produce losses in the milk coagulating activity of the microbial rennet. The following values of activity, based on 100 percent activity of untreated microbial rennet, were obtained after treatment with 0.1 and 2.0 percent (w/v) anhydride, respectively: isatoic anhydride, 33 and 2 percent; trans-1,2-cyclohexanedicarboxylic anhydride, 92 and 62 percent; itaconic anhydride 94 and 68.8 percent; dl-camphoric anhydride, 98 and 79 percent; 2,3-dimethylmaleic anhydride, 92.5 and 67.4 percent. In general, the lowest loss of activity occurred at the lowest concentrations of anhydride, e.g., 0.1 percent w/v, while the highest loss in activity occurred at the highest concentrations, 2 percent w/v. These test results, in conjunction with the test results described in Examples 1-3, indicate that acylation of *Mucor pusillus* microbial rennet has a highly selective and unpredictable effect on the enzyme's milk coagulating activity.

Further comparative tests were carried out to determine the effect of acylation on milk coagulating activity of *Mucor miehei* microbial rennet.

COMPARATIVE EXAMPLE A

A solution of about 9.3 percent strength *Mucor miehei* microbial enzyme was prepared by adding microbial rennet powder, (assay 2322 percent) to 250 ml of 0.2 M sodium phosphate buffer (pH=7.0). The microbial rennet powder was obtained from a crude fermentation broth of the *Mucor miehei* by polyacrylic acid coprecipitation and decomposition of the resulting complex with calcium ion (See *Process Biochemistry*, pp. 11-12, September 1976). Twenty ml-aliquots of this solution were cooled to 0°-5° C. in an ice-water bath with stirring and adjusted to pH 7.5 with concentrated sodium hydroxide. The aliquot portions were maintained at a pH of about 7.5 by titration with sodium hydroxide and reacted incrementally with increasing amounts of maleic anhydride.

The milk coagulating activity of this acylated *Mucor miehei* rennet was determined and compared with untreated *Mucor miehei*. The experimental results obtained are summarized in Table 4 below.

TABLE 4

Reaction of *Mucor miehei* Microbial Rennet Enzyme with Maleic Anhydride at 5° C.

| Sample | Anhydride Added (mg) | Increments of Anhydride Added | Assay Time (sec) | % Original Activity |
|---|---|---|---|---|
| 35 | 0 | 0 | 43 | 100 |
| 36 | 20 | 1 × 20 mg | 49 | 88 |
| 37 | 50 | 1 × 50 mg | 52 | 83 |
| 38 | 100 | 1 × 100 mg | 52 | 83 |
| 39 | 200 | 2 × 100 mg | 53 | 81 |
| 40 | 400 | 4 × 100 mg | 56 | 77 |
| 41 | 800 | 8 × 100 mg | 171 | 25 |

The above results indicate that acylation of *Mucor miehei* microbial rennet enzyme with maleic anhydride produces a decrease in the milk coagulating activity of the rennet. This is in contrast to the increase in milk coagulating activity of microbial rennet enzyme from *Mucor pusillus* treated with maleic anhydride, described in Examples 1 and 2.

What is claimed is:

1. A method for increasing the milk coagulating activity of microbial enzyme obtained from *Mucor pusillus* micro-organisms comprising acylating in an aqueous medium said enzyme by contacting the *Mucor pusillus* microbial rennet enzyme at a temperature of about 0° to 25° C. and a pH of about 5 10 with from 0.1 to 2 percent (w/v) based on enzyme volume of an acylating agent selected from the group consisting of maleic, citraconic, phthalic, cis-1,2-cyclohexanedicarboxylic, 1,2,4-benzenetricarboxylic, homophthalic, 3-nitrophthalic, bromomaleic and dichloromaleic anhydride for a time sufficient to obtain said desired increase.

2. A method as claimed in claim 1 wherein the acylating agent is maleic anhydride.

* * * * *